United States Patent [19]

Brock

[11] Patent Number: 4,745,927
[45] Date of Patent: May 24, 1988

[54] ORTHOPEDIC SHOE CUSHION INSERT APPARATUS AND A METHOD OF PROVIDING SAME

[76] Inventor: N. Lee Brock, 1623 W. El Rio Dr., Apt. 144, Tucson, Ariz. 85745

[21] Appl. No.: 906,832

[22] Filed: Sep. 12, 1986

[51] Int. Cl.[4] .............................................. A43B 7/26
[52] U.S. Cl. .................................... 128/581 R; 36/94; 128/81 R
[58] Field of Search ................. 128/81 R, 180 D, 581, 128/595, 596; 36/94, 96; 2/22

[56] References Cited

U.S. PATENT DOCUMENTS

| | | | |
|---|---|---|---|
| 1,098,397 | 6/1914 | Pecorella | 128/81 R |
| 1,167,019 | 1/1916 | Reed | 128/81 R |
| 1,746,865 | 2/1930 | Page | 128/81 R |
| 2,096,500 | 10/1937 | McCahan et al. | 36/94 X |
| 2,507,120 | 5/1950 | Shapiro | 128/81 R X |
| 2,721,403 | 10/1955 | Quisling | 128/581 X |
| 2,780,013 | 2/1957 | Voss | 128/581 X |
| 3,066,678 | 12/1962 | Riecker | 128/81 R X |
| 3,275,002 | 9/1966 | Scholl | 128/581 |
| 4,227,320 | 10/1980 | Borgeas | 128/80 D X |
| 4,563,787 | 1/1986 | Drew | 128/581 X |

FOREIGN PATENT DOCUMENTS

| | | | |
|---|---|---|---|
| 265500 | 10/1913 | Fed. Rep. of Germany | 36/94 |
| 267325 | 3/1927 | United Kingdom | 128/81 R |
| 596343 | 1/1948 | United Kingdom | 36/94 |

*Primary Examiner*—Edgar S. Burr
*Assistant Examiner*—Moshe I. Cohen
*Attorney, Agent, or Firm*—Harry M. Weiss & Assoc.; Victor Flores

[57] ABSTRACT

An orthopedic shoe cushioned insert having a cushioned plate member with a first and second attachment means and a method of operation thereof are disclosed. Here, the cushioned plate member is comprised of an upper and a lower plate member being attached together preferably with a two-sided tape therebetween, as well as providing a cushion effect thereof. The first attachment means is coupled therebelow the bottom front portion of the lower plate member for suitably wrapping around an ailing or injured toe. The second attachment means is coupled therebelow the bottom back portion of the lower plate member for suitably wrapping around a foot. The orthopedic shoe cushioned insert is reversible; i.e., usable for either a right or left foot, as well as effective for managing arthritic ailments of toes or joints thereof, such as "halux rigidus", or the like.

9 Claims, 1 Drawing Sheet

U.S. Patent May 24, 1988 4,745,927
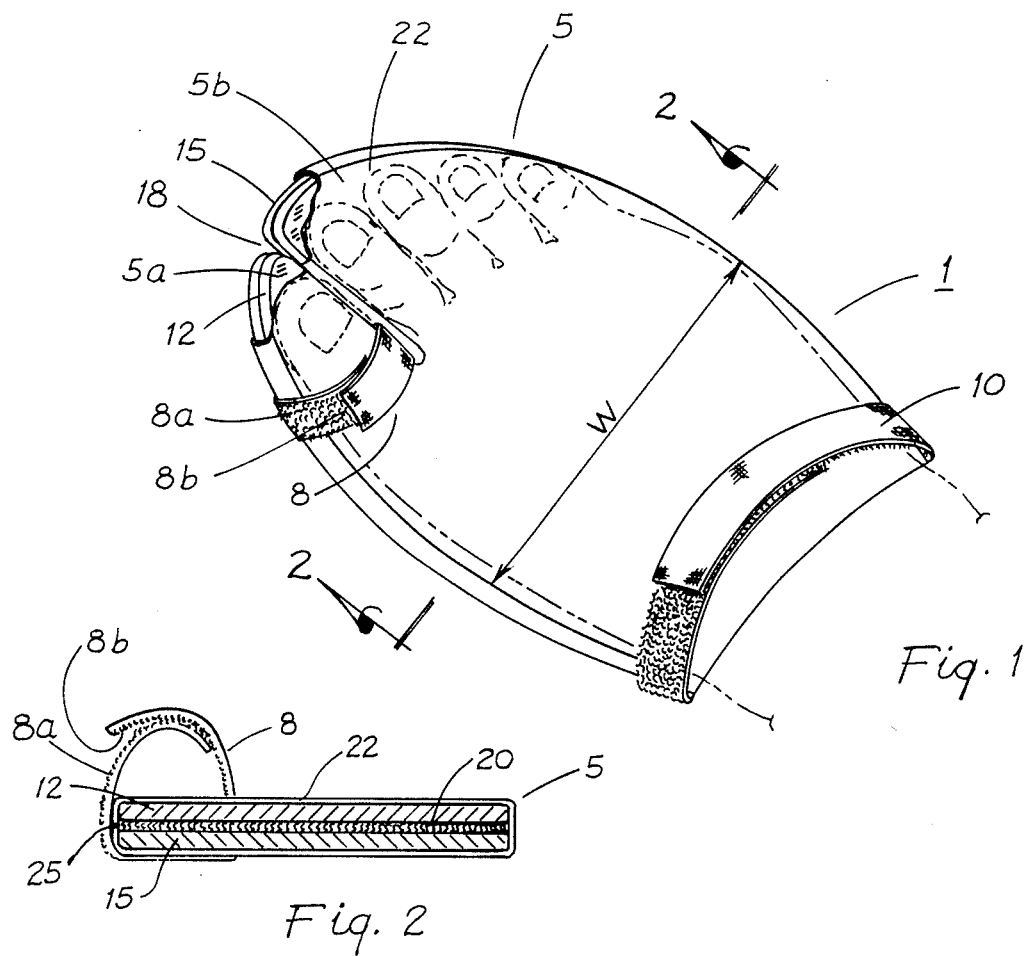
Fig. 1
Fig. 2
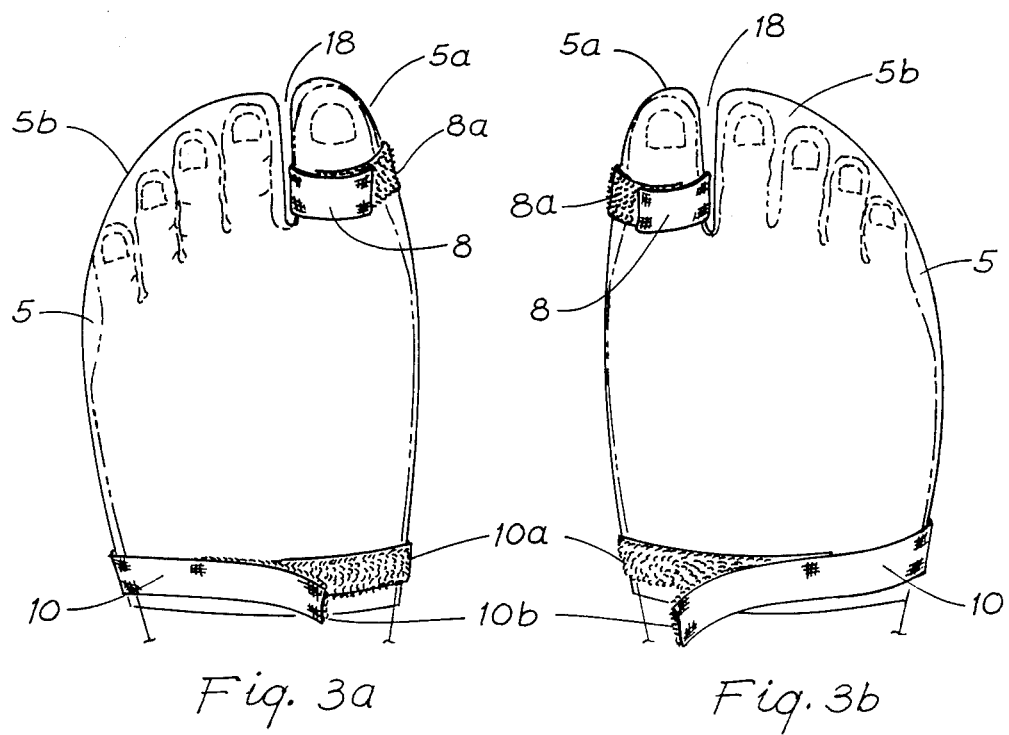
Fig. 3a
Fig. 3b

ORTHOPEDIC SHOE CUSHION INSERT APPARATUS AND A METHOD OF PROVIDING SAME

BACKGROUND OF THE INVENTION

1. Field of the Invention

This invention generally relates to an orthopedic shoe cushion insert apparatus and a method of providing same. More particularly, the invention relates to a shoe insert apparatus which may be worn on either foot by a person suffering from an arthritic toe condition and which is positioned beneath a wearer's forefoot and thereat be attached such that a wearer's great toe is immobilized and the adjoining lesser toe's movement is limited and thereby achieving arthritic pain relief.

2. Description of the Relevant Art

There has been a substantial need for supporting an ailing or injured foot or any part thereof. Many devices have been provided in attempts to manage the treatment of an ailing or injured foot or any part thereof by providing, for example, a bent plate with a loop to enclose a toe joint, as in U.S. Pat. No. 933,423, filed Sept. 3, 1908 and issued to W. H. De Ford on Sept. 7, 1909, for shielding a foot from the inside surface of a shoe in order to reduce an existing bunion. See also, U.S. Pat. No. 1,098,397, filed May 24, 1915 and issued to B. Crowe on Mar. 14, 1916. Here, however, it is clear that the De Ford and Crowe devices are for the specific use of shielding an occurring bunion from the inner surface of the shoe. Moreover, the De Ford and Crowe patents disclose a bent support plate for use only with one foot; thus requiring one device for a right foot an another for a left foot, as well as lacking any cushioning effect when in use.

In U.S. Pat. No. 3,299,894 filed July 8, 1964 and issued to J. N. A. Charlebois on Jan. 24, 1967 and in U.S. Pat. No. 1,098,397 filed Nov. 21, 1913 and issued to A. Pecorella on June 2, 1914 (see also, U.S. Pat. No. 1,554,883 filed Feb. 5, 1923 and issued to M. Sahlin on Sept. 22, 1925), a plate member having a plurality of loops on the front thereof for alleviating perspiration problems and for straightening out crooked toes, respectively. In either the Charlebois or the Pecorella patent (see also, the Sahlin patent), no mention is made in the need to immobilize any part of the foot or toe thereof or any associated joints thereof. Moreover, these patents cannot be used for either foot nor do they provide any cushioning effect therebelow the foot or any part thereof.

In U.S. Pat. No. 2,633,129 filed Feb. 28, 1950 and issued to C. F. Crawford on Mar. 31, 1953, a foot cushioning device is shown with a toe engaging loop extending therefrom for placing the foot cushion below the foot. Here, the toe engaging loop is not used for immobilizing an ailing or injured toe, but merely to set the cushion device below the foot. In U.S. Pat. No. 2,711,166 filed Sept. 18, 1953 and issued to J. S. Digate on June 21, 1955, a surgical pad device is disclosed, but again lacking any associated feature for immobilizing an ailing or injured toe, such as an arthritic toe, or any joints thereof, such as an arthritic toe, for allowing the immobilized toe to heal and further permit the person to walk therewith.

From the foregoing prior art teachings and from unavailability in commercial literature it is observed that there is a need for a device which may be inserted in a shoe and by design cause arthritic pain relief in any of the toes.

It is therefore an object of the present invention to provide an orthopedic shoe cushioned insert which can effectively relieve pain in an injured or ailing toe, such as an arthritic toe ailment of "halux rigidus" or the like, and consequently avoid painful alternative remedies, such as surgery, corrective shoes or the like.

It is another object of the present invention to provide an orthopedic shoe cushion insert having at least two plate members with a tape member therebetween for cushioning and attaching thereof.

It is another object of the present invention to provide an orthopedic shoe cushioned insert having at least two plate members with an alternative cushioning member therebetween.

It is yet another object of the present invention to provide an orthopedic shoe cushioned insert having a slit portion which provides a support portion for the great toe and another support portion for the lesser toes and at least one removable front attaching member for removably wrapping around the great toe.

It is yet another object of the present invention to provide an orthopedic shoe cushioned insert having at least one removable back attaching member for removably wrapping around an adjoining forefoot.

It is a further object of the present invention to provide an orthopedic shoe cushioned insert suitable for being properly sized to accommodate thereon any sized foot.

It is a further object of the present invention to provide an orthopedic shoe cushioned insert suitable for being reversed for being used for either a right or left foot.

It is still a further object of the present invention to provide an orthopedic shoe cushioned insert which can be easily and economically produced, yet sturdy in construction and highly efficient in use.

It is still a further object of the present invention to provide an orthopedic shoe cushioned insert which is constructed with relative simplicity, embodying relatively simple parts, and therefore capable of being retailed for a low price, long-lasting in use, and extremely convenient to use.

SUMMARY OF THE INVENTION

The aforementioned and other objects of the present invention are accomplished by providing a properly foot-fitted plate having at least two plate members with a cushioned member therebetween, preferably a two-sided tape member therebetween. At the front of the foot-fitted plate is a slit portion for dividing the front of the plate into a first support portion for the great toe and a second support portion for the lesser toes. This slit portion allows the placement of a removable attachment member suitable for bracing and immobilizing a great toe. At the back portion of the foot fitted plate is a removable attachment member suitable for securing the foot-fitted plate to the forefoot. The orthopedic shoe cushioned insert can be reversible for use for a right or left foot and suitable for being accommodated in a slipper or a shoe. The orthopedic shoe cushioned insert is specially useful and effective in the management of treating an arthritic condition of a big toe, especially with person's having an arthritic condition, called "halux rigidus", or the like and to effectively avoid painful treatment alternatives, such as surgery, corrective shoes, or the like.

BRIEF DESCRIPTION OF THE DRAWINGS

FIG. 1 is a perspective view of the orthopedic shoe cushioned insert shown in use, without a shoe, on the right forefoot of a wearer and also showing in a cutaway view, the upper and lower plate arrangement at the frontal slit portion, also shown are the front and back attachment members and a variable width option of the present invention;

FIG. 2 is a cross-sectional view taken along line 2—2 of FIG. 1 showing the arrangement of the covering means, the cushioning means therebetween the upper and lower plates and a typical right-handed fastening arrangements of the front attachment member, shown as "VELCRO" strips, of the present invention;

FIGS. 3a and 3b are top elevational views of the orthopedic shoe cushioned insert shown in use without shoes on left and right forefeet of a wearer, respectively, of interest is the reversibility accomplished by flipping the cushioned plate member and reinstalling to accommodate right or left forefoot use and further showing the right or left hand fastening flexibility resulting due to removable front and back attachment members, shown as, "VELCRO" strips with mating surfaces oriented accordingly.

DETAILED DESCRIPTION OF THE PREFERRED EMBODIMENTS

The present invention is a shoe insert device which is intended to be worn by a person who is suffering from an ailing arthritic condition in the toes. It is well known that if the joints affected with arthritis are immobilized, the pain associated with the arthritic condition will be relieved. The device in its preferred embodiment is a cushioned plate member provided in the shape of the bottom of the forefoot and outlines the toes and front part of the arch of the foot and has a slit in the front portion, whereby the cushioned plate member is divided to provide a first support portion for the great toe and a second support portion for the lesser toes. The slit portion further provides a means for allowing a removable attachment member to couple a wearer's great toe to the first support portion on the cushioned plate member whereby the great toe is immobilized. Having immobilized the great toe, using this invention, it has been observed, that the lessor toes on the second support portion have concurrently had their movement limited by the insert device. The insert is intended to be held in place beneath the wearer's forefoot by the first attachment member, as described above, and also by a back attachment member wrapped around the bottom back-end of the insert and the upper part of the forefoot. The device may be used on either foot by merely locating the great toes's first support portion on the cushioned plate member and positioning beneath the forefoot of the selected foot. The removable straps, in particular, the "VELCRO" strips, offer the user the flexibility to choose the orientation of fastening depending on whether the wearer is right or left handed.

The material chosen for the cushioned plate member, along with the material chosen for the cushioning means must result in a semi-rigid structure which is comfortable for wearing as a shoe insert without impairing walking capability of the wearer, yet will immobilize the arthritic toes of the wearer and relieve pain. For example the upper and lower plate members could be made from a substantially thin gauge steel with an inner cushion being double-sided tape, or the like.

Referring to FIG. 1, there is shown a perspective view of the insert apparatus, generally referred to as 1, being worn on a right forefoot of a wearer. The insert device is preferably provided in various width W to accommodate the various widths of the wearers. The insert apparatus 1 is comprised of a cushioned plate member 5 having a slit portion 18 located frontward and serves to divide plate member 5 into a first support portion 5a and a second support portion 5b for the lessor toes. As is best seen from FIG. 2, the cushioned plate member 5 is comprised of a lower plate 15, and upper plate 12 and a cushion means 20 installed therebetween plate 12 and 15. The cushioned plate member 5 is provided with a replaceable covering 22 having a connecting seam 25 along the edges of the upper and lower plates 12 and 15, respectively. As can be seen from FIGS. 1, 3a and 3b, the attachment to a wearer's forefoot is done by positioning a removable first attachment member 8, which is preferably "VELCRO" strips, through slit 18, around the first support portion 5a and then around the wearer's great toe. In the preferred embodiment, having attachment member 8 replaceable, gives fastening flexibility to the user by allowing proper position of mating surfaces 8a and 8b for right or left hand fastening. The back part of cushioned plate member 5 is attached to the wearer's forefoot using a second attachment member 10 having mating surfaces 10a and 10b. FIGS. 3a and 3b shows the insert apparatus 1 in use on a wearer's right and left forefeet. With first attachment member 8 and second attachment member 10 coupling a wearer's great toe and forefoot, the cushioned plate member 5 is firmly positioned below a wearer's forefoot and will effectively immobilize the great toe and substantially limit movement of the lesser toes to relieve arthritic pain in any of the wearer's toes, especially the great toe which is immobilized.

While the invention has been particularly shown and described in reference to preferred embodiments thereof, it will be understood by those skilled in the art that changes in form and details may be made without departing from the spirit and scope of the invention.

I claim:

1. An orthopedic shoe insert device for immobilizing a wearer's arthritic toes, or any joint thereof, said device comprising:
   (a) a cushioned, semi-rigid plate member means for supporting a wearer's forefoot area, especially including arthritic toes, said cushioned plate member means having a frontal slit portion defining a first support portion for supporting a wearer's great toe and a second support portion for supporting a wearer's lesser toes, said cushioned plate member means includes:
   an upper plate member means,
   a lower plate member means and
   a cushioning means positioned between said upper plate member means and said lower plate member means; said upper and lower plate member means being made out of a durable, semi-rigid material selected from the group consisting of metal and plastic;
   (b) a first attachment means, removably coupled around said first support portion, for firmly wrapping said wearer's great toe and thereby immobilizing said great toe and substantially limiting movement of said lesser toes and relieving arthritic pain in any of said wearer's toes, especially the great toe which is immobilized; and (c) a second attachment means, removably coupled around a back portion of said cushioned plate member means, for firmly wrapping around said wearer's forefoot and thereby firmly retaining said shoe insert device beneath said wearer's forefoot said cushioned plate member means being provided for use on either of said wearer's forefeet by flipping said cushioned plate member and reinstalling said first and second attachment means.

2. An orthopedic shoe insert device for immobilizing a wearer's arthritic toes, as recited in claim 1, wherein:
said removably coupled first attachment means is a "VELCRO" strip member means having mating ends firmly mating above said wearer's great toe, at a joint thereof, said "VELCRO" strip member being removably coupled to allow locating said mating ends for easy attachment by a right-handed or left-handed wearer.

3. An orthopedic shoe insert device for immobilizing a wearer's arthritic toes, as recited in claim 1, wherein:
said removably coupled second attachment means is a "VELCRO" strip member means having mating ends firmly mating above said wearer's forefoot, said "VELCRO" strip member being removably coupled to allow locating said mating ends on an appropriate side for easy attachment by a right-handed or left-handed wearer.

4. An orthopedic shoe insert device for immobilizing a wearer's arthritic toes, as recited in claim 1, wherein:
said cushioning means comprises a two-sided tape member.

5. An orthopedic shoe insert device for immobilizing a wearer's arthritic toes, as recited in claim 1, further comprising:
an external, replaceable, covering member for providing a soft, cloth-like surface between said cushioned plate member means and the bottom of said wearer's forefoot, said covering member means being provided on both sides of said cushioned plate member and providing a connecting portion between said upper and lower plate member means.

6. An orthopedic shoe insert device for immobilizing a wearer's arthritic toes, as recited in claim 1, wherein:
said cushioned plate member means conforms substantially to the shape of said wearer's forefoot.

7. An orthopedic shoe insert device for immobilizing a wearer's arthritic toes, or any joint thereof, said device comprising:
(a) a cushioned, semi-rigid plate member means for supporting a wearer's forefoot area, especially including arthritic toes, said cushioned plate member means having a frontal slit portion defining a first support portion for supporting a wearer's great toe and a second support portion for supporting a wearer's lesser toes, said cushioned plate member means conforming substantially to the shape of said wearer's forefoot, said cushioned plate member means includes:
an upper plate member means,
a lower plate member means and
a cushioning means positioned between said upper plate member and said lower plate member, said cushioning means being a two-sided tape member, said upper and lower plate member means being made out of a durable, semi-rigid material selected from the group consisting of metal and plastic;

(b) a first attachment means, removably coupled around said first support portion, for firmly wrapping said wearer's great toe and thereby immobilizing said great toe and substantially limiting movement of said lesser toes and relieving arthritic pain in any of said wearer's toes, especially the great toe which is immobilized, said first attachment means being a "VELCRO" strip member means having mating ends firmly mating above said wearer's great toe, at a joint thereof, said "VELCRO" strip member being removably coupled to allow locating said mating ends for easy attachment by a right-handed or left-handed wearer;

(c) a second attachment means, removably coupled around a back portion of said cushioned plate member means, for firmly wrapping around said wearer's forefoot and thereby firmly retaining said shoe insert device beneath said wearer's forefoot, said second attachment means being a "VELCRO" strip member means having mating ends firmly mating above said wearer's forefoot, said "VELCRO" strip member being removably coupled to allow locating said mating ends on an appropriate side for easy attachment by a right-handed or left-handed wearer said cushioned plate member means being provided for use on either of said wearer's forefeet by flipping said cushioned plate member means and reinstalling said first and second attachment members; and (d) an external, replaceable, covering member for providing a soft, cloth-like surface between said cushioned plate member means and the bottom of said wearer's forefoot, said covering member being provided on both sides of said cushioned plate member and providing a connecting portion between said upper and lower plate members.

8. A method of providing an orthopedic shoe insert device for immobilizing a wearer's arthritic toes, or any joint thereof, said method comprising the steps of:
(a) providing a cushioned, semi-rigid plate member means for supporting a wearer's forefoot area, especially arthritic toes including:
(i) providing an upper plate member means,
(ii) providing a lower plate member means and
(iii) providing a cushioning means fixedly positioned between said upper plate member means and said lower plate member means and thereby joining said upper and lower plate member means;

(b) providing an external, replaceable, covering member on both sides of said plate member means and providing a connecting portion between said upper and lower plate member means;

(c) providing a frontal slit portion on said plate member means defining a first support portion for supporting a wearer's great toe and a second support portion for supporting a wearer's lesser toes, said plate member means conforming substantially to the shape of said wearer's forefoot;

(d) providing a first attachment means, removably coupled around said first support portion;

(e) providing a second attachment means, removably coupled around a back portion of said plate member means;

(f) firmly wrapping said wearer's great toe using said first attachment means and thereby immobilizing said great toe and substantially limiting movement of said lesser toes and relieving arthritic pain in any of said wearer's toes, especially the great toe which is immobilized;

(g) firmly wrapping around said wearer's forefoot using said second attachment means and thereby firmly retaining said shoe insert device beneath said wearer's forefoot; and (h) inserting a wearer's foot with said shoe insert firmly positioned beneath said wearer's forefoot into a shoe apparel.

9. A method of providing an orthopedic shoe insert device for immobilizing a wearer's arthritic toes as recited in claim 8 wherein:

(a) said cushioning means is a two-sided tape member;

(b) said upper and lower plate member means are made out of a durable, semi-rigid material selected from the group consisting of metal and plastic;

(c) said external covering means is a soft, cloth-like material;

(d) said first attachment means is a VELCRO strip suitably sized for wrapping around said wearer's great toe and said first support portion; and (e) said second attachment means is a VELCRO strip suitably sized for wrapping around said wearer's forefoot and a back portion of said plate member means.

* * * * *